United States Patent [19]

Meyers et al.

[11] 4,361,435

[45] Nov. 30, 1982

[54] COPPER AND AMINE BASED AQUATIC HERBICIDES

[75] Inventors: Marion D. Meyers; Graham A. Stoner, both of Houston, Tex.

[73] Assignee: Sandoz, Inc., East Hanover, N.J.

[21] Appl. No.: 935,594

[22] Filed: Aug. 21, 1978

Related U.S. Application Data

[63] Continuation of Ser. No. 443,493, Feb. 19, 1974, abandoned.

[51] Int. Cl.$^3$ .................. A01N 33/04; A01N 59/20
[52] U.S. Cl. .................................. 71/66; 71/65; 71/67; 71/88; 71/92; 71/97
[58] Field of Search .................................. 71/66, 67

[56] References Cited

U.S. PATENT DOCUMENTS

| | | | |
|---|---|---|---|
| 2,400,863 | 5/1946 | Gelfand | 71/67 |
| 2,734,028 | 2/1956 | Domogalla | 71/67 |
| 2,878,155 | 3/1959 | Cruickshank | 71/67 |
| 3,318,870 | 5/1967 | Teumac | 71/66 |
| 3,512,954 | 5/1970 | Keckemet | 71/66 |
| 3,634,061 | 1/1972 | Geiger et al. | 71/67 |
| 3,930,834 | 1/1976 | Schulteis et al. | 71/67 |

OTHER PUBLICATIONS

Vishnyakova et al., "Effect of Compounds Containing, etc.," (1972) CA77, No. 1232d. (1972).
Hall et al., "Polarographic Study of the Complexes, etc." (1972).
Laura et al. "Adsorption of EDA on Montmorillonite, etc.," (1970)
Wilson et al., "Botany" (1962).
Holt, Rinehart & Winston, N.Y., Chicago etc., pp. 334,335,356,357 (1962).

*Primary Examiner*—Glennon H. Hollrah
*Attorney, Agent, or Firm*—Gerald D. Sharkin; Richard E. Vila

[57] ABSTRACT

Herbicidal and algaestatic and algaecidal compositions and use thereof comprising copper salts; both soluble acid salts as copper sulfate, chloride, nitrate, acetate, sulfamate, gluconate, citrate, etc. and basic copper salts such as basic copper sulfate, cupric hydroxide, basic copper carbonate, basic copper chloride and the like for a method for treating bodies of water to arrest or eliminate the growth of algae and aquatic weeds by giving a more efficient algaestat, algaecide and/or herbicide, when the copper salts or insoluble basic copper salts are used as a complex with an alkylene diamine, such as ethylenediamine, propylenediamine and substituted derivatives of these; or poly (aminoalkylene)$_n$—NH$_2$ wherein n is from 2 to 4, 5 or 6 such as diethylene triamine, triethylene tetraamine, tetraethylene pentaamine, dipropylene triamine, or mixtures of each of these with the others, including diamines, such as aminoethyl ethanolamine and mixtures of same with the other amines; in the complex a high copper content in useful form is achieved and the effect of the complex on the weeds is prolonged and noteworthy; as against previous copper compounds which require the use of an organic herbicide such as 1,1' ethylene-2,2' dipyridinium dibromide, (DIQUAT$^R$) with the copper compound to produce satisfactory herbicidal action at safe and economic copper levels, the herein disclosed and claimed copper and alkylene diamine complex is used alone for aquatic weed control.

15 Claims, No Drawings

COPPER AND AMINE BASED AQUATIC HERBICIDES

This is a continuation of application Ser. No. 443,493 filed Feb. 19, 1974, now abandoned.

This invention relates to an algaecide and aquatic weed herbicide composition and, more particularly, to an algaecide and aquatic weed herbicide composition of copper salts and copper salts as a complex either as the water soluble acid or insoluble basic compounds with an alkylene diamine, triamine, tetraamine or pentaamine.

BACKGROUND FOR THE INVENTION

Numerous bodies of water such as rivers, lakes, ponds, streams, brooks, drinking water supplies, irrigation systems, agricultural water systems, fish ponds, swimming pools, shower rooms and industrial water systems, such as cooling towers and ponds, are frequently polluted by an excessive growth of algae and other microorganisms which impart an unacceptable quality to the body of water. Moreover, some of the enumerated bodies of water develop excessive aquatic weed growth which interferes with the flow of water and renders the body of water unsuitable for the intended use or diminishes the economic value of it. The particularly noxious aquatic weed of economic importance is *Hydrilla Verticillata*, which is commonly controlled by application of copper materials along with an organic herbicide such as 1,1'-ethylene-2,2'-dipyridinium dibromide. Weeds and algae in the recited bodies of water are controlled by various means including chemical algaestats, algaecides and herbicides. Not all of the chemicals used are fully effective algaecides and few have useful herbicide properties and then only against limited numbers of weeds.

THE PRIOR ART

For the control of the algae, the prior art has used, with considerable success, acid or water soluble salts of copper as inorganic or organic salts, e.g., copper sulfates, chlorides, bromides, acetates, nitrates, citrates or the like. The inorganic acid copper salts are disclosed in U.S. Pat. No. 2,734,028 and are used in the form of a complex with an alkanolamine; the acid salts of copper compounds reacted with aliphatic hydroxy acids are disclosed in U.S. Pat. No. 2,400,863.

However, the stability of the copper salt and its complex has left much to be desired and further improvements have been shown in U.S. Pat. No. 3,716,351 which patent discloses an algaecide composition containing a complex of a water soluble salt with an alkanolamine and stabilizers therefor. For stabilizing the copper salts against decomposition to elemental copper and/or cuprous oxide in storage in the last mentioned patent, it has been taught that an effective amount of an acetylenic diol and an alkali metal halogenate prevents the copper alkanolamine complex from decomposing during the periods of storage. In U.S. Pat. No. 3,716,351 it has been mentioned specifically that the additives are for preventing the complex from decomposing during extended periods of storage.

Further, in U.S. Pat. No. 2,734,028, it has been mentioned that in alkaline waters with a pH over 7 (and, particularly, in waters containing carbonates or bicarbonates), the copper sulfate is generally ineffective due to the waste caused by precipitation of copper in the form of either insoluble copper hydroxide or copper carbonate.

Still further, while the composition described in U.S. Pat. No. 2,734,028 has been alleged to be useful as a herbicide, the amount of the composition which has to be used to achieve the desired results make it uneconomical or unduly toxic and hence unacceptable except for a limited number of weeds (cf. Sutton et al., "Uptake of Copper in Hydrilla", *Weed Res.*, Vol. 11, Page 47 (1971)). Another improvement in a prior art copper algaecide has been disclosed in a companion application Ser. No. 397,136 filed Sept. 13, 1973. For example, to control *Hydrilla Verticillata*, the amount of copper compound used can be decreased to an economic level when the copper compound is used in combination with another herbicide such as the organic 1,1' ethylene-2,2' dipyridinium dibromide (cf. Sutton et al., "Effect of DIQUAT on Upstake of Copper in Aquatic Plants", *Weed Sci.*, Vol. 18, Page 703 (1970)).

BRIEF DESCRIPTION OF THE INVENTION

It has now been found that contrary to the prior art teaching, the use of basic copper salts such as cupric hydroxide, base copper carbonate, basic copper chloride, basic copper sulfate and the like and acid copper salts such as copper sulfate, copper chloride, etc. results in unexpectedly beneficial composition for a method for treating the enumerated bodies of water to arrest or eliminate the growth of algae and aquatic weeds by giving a more efficient algaecide and herbicide, when the water soluble acid copper salts or insoluble basic copper salts are used as a complex with an alkylene diamine, such as ethylenediamine, propylenediamine, N-methyl ethylenediamine, N,N'-dimethyl-1,3, propanediamine, N-methyl,1,3-propanediamine, N,N,N'N'-tetraethylethylenediamine, or poly(aminoalkylene)$_n$—$NH_2$ wherein n is from 2 to 4 or 5 such as diethylene triamine, triethylene tetraamine, tetraethylene pentaamine, or mixtures of each of these with the others. Other useful diamines are aminoethyl ethanolamine and mixtures of it with the other amines. The improved herbicidal action of the disclosed complex is especially noteworthy, more so, because solutions of this complex can be used in practical economical and ecologically safe amounts without additional herbicidal compounds as required when using copper salts or complexes as in the prior art.

Still further, the same high copper content is achieved and the effect of the complex on the weeds is prolonged and noteworthy. (Table I).

TABLE I

| | CONTROL OF HYDRILLA VERTICILLATA WITH DIFFERENT COPPER MATERIALS[a] | | | | |
|---|---|---|---|---|---|
| | | | Percent Control at Different Copper Rates After Exposure | | |
| | | | 2 Weeks | | 4 Weeks |
| Copper Source[b] | | % Cu | 0.1 ppm Cu | 0.4 ppm Cu | 0.1 ppm Cu | 0.4 ppm Cu |
| Copper Sulfate-EDA Solution | | 8 | 7 | 45 | 17 | 78 |
| Copper Hydroxide-TEA[e] Solution | | 8 | 0 | 17 | 0 | 40 |

TABLE I-continued
CONTROL OF HYDRILLA VERTICILLATA WITH DIFFERENT COPPER MATERIALS[a]

| | | Percent Control at Different Copper Rates After Exposure | | | |
|---|---|---|---|---|---|
| | | 2 Weeks | | 4 Weeks | |
| Copper Source[b] | % Cu | 0.1 ppm Cu | 0.4 ppm Cu | 0.1 ppm Cu | 0.4 ppm Cu |
| Copper Sulfate-TEA Solution | 7.1 | 0 | 5 | 5 | 20 |
| Copper Sulfate Pentahydrate Crystals | 25.2 | 0 | 5 | 0 | 23 |
| Copper Carbonate (MALACHITE) | 55 | 0 | 0 | 0 | 0 |
| Copper Hydroxide-TEA Solution + DIQUAT | 8 | 8[c] | 78[d] | 37[c] | 89[d] |

[a]Experiments conducted in a controlled, environmental laboratory.
[b]Ethylenediamine = EDA
[c]0.25 ppm Cu and 0.1 ppm DIQUAT used
[d]0.5 ppm Cu and 0.1 ppm DIQUAT used.
[e]Triethanolamine

DISCUSSION OF THE INVENTION

As an alkylene amine useful in the present formulation of the copper complex compositions, di-, tri-, tetra or penta amines having from 2 to 4, 5 or 6 carbon atoms in the alkylene group are employed as well as amino alkylalkanol amines having from 2 to 4 or 5 carbon atoms in the alkyl and alkanol group, e.g., amino ethyl ethanol amine. These di- and tri-, tetra-, and pentaamines consist of ethylene diamine (EDA), diethylene triamine, triethylene tetraamine, tetraethylene pentaamine; propylene diamine, dipropylene triamine and the like as well as mixtures of these and, in addition, N-alkyl substituents of said amines. The preferred compound is ethylene diamine and the preferred combination of it is with copper sulfate pentahydrate or basic copper salt, such as copper hydrate or copper hydroxide. A formulation for the copper salt complex with the alkylene diamine or the other amines can range from a ratio of 1:1 to 10:1 amine to copper based on the number ratio of the copper salt and the amine molecules; it has been found that a formulation of copper with ethylene diamine with an amine to copper ratio of 2:1 is very acceptable.

A complex of copper (II) with two moles of ethylene diamine is chemically stable (stability constant, log K=20.03) and thus is a useful complex in the control of algae and weeds.

Of the basic copper salts, various forms of copper hydroxide $(Cu(OH)_2)$ (cupric) have been found to be the most advantageous. Copper hydroxide is synonymous with cupric hydroxide, copper hydrate, hydrated copper oxide, etc. The copper alkylene di-amine complex is prepared by dissolving copper hydroxide or hydrated copper oxide in an aqueous solution of one of the above recited alkylene amines.

A water soluble di, tri, tetra or pentaamine is required or the reaction product (complex) must be water soluble.

A representative reaction of the copper compound and amine is depicted as follows

$$Cu^{++} + 2H_2NCH_2CH_2NH_2 + 2H_2O \rightarrow [Cu(H_2NCH_2CH_2NH_2)_2(H_2O)_2]^{++}$$

In the examples to follow various embodiments of the invention are illustrated.

EXAMPLE 1

One mole of copper sulfate pentahydrate (CSP) crystals was reacted with two moles of reagent grade 91–93% ethylenediamine (EDA diluted with water). The reaction was very exothermic and copper sulfate pentahydrate was added stepwise during 30 minutes to keep the temperatures below 70° C. The dark purple solution was diluted with water to 7% copper. The properties of the solution were: pH 11.5; 1.182 specific gravity at 25° C.; and 13.6 cps viscosity at 25° C.

EXAMPLE 2

To the Cowles dissolver were added 150 gallons of water and one drum 414 pounds, of 99% ethylenediamine. The temperature of the stirred solution was 56° C. Stirring was continued as 400 pounds of copper sulfate pentahydrate (CSP), crystals (100% through 30 mesh and 95% retained on 100 mesh screen) were added over a period of five minutes; the temperature rose to 68° C. One hundred pound quantities of CSP crystals were added at one-half hour intervals until a total of 860 pounds were used. The calculated EDA:Cu molar ratio was 1.998:1 based on copper analysis of 25.19% for the CSP crystals. Solution pH was 8.0 after the addition of 26 gallons of water and 11 pounds 99% EDA and further stirring for 15 minutes, the copper content was 8.12% with specific gravity 1.224 at 25° C., pH 10.6. A total of 240 gallons of product was packaged in five gallon containers. Summary of the analytical and physical data for the solution of the complex is in the following Table II.

TABLE II
PROPERTIES OF (BIS-ETHYLENEDIAMINE) COPPER SULFATE FOR EXAMPLE 2

| Analyses | Actual | Calculated[a] |
|---|---|---|
| Cu | 8.12% | 8.00% |
| C | 6.48% | 6.05% |
| H | 9.32% | 9.28% |
| N | 7.31% | 7.05% |
| SO$_4$ | 11.13$_b$% | 12.08% |
| pH | 10.6% | — |
| Density, 25° C. | 1.224 gm/cc | — |
| Viscosity, 25° C. | 14.5% cps | — |
| Color | Deep Purple | — |

[a]Based on aqueous solution containing 8% metallic copper and molar ratio of 2:1 amine to copper.
[b]Based on total sulfur content of 3.71 percent.

Crystals of bis(ethylenediamine) copper (II) sulfate were precipitated in 100% yield from an 8% solution by the addition of five volumes of 95% ethanol. The crystals were isolated by filtration; the resulting filtrate was colorless and free of copper. The product was dried overnight in a vacuum oven at 30° C. Analysis for copper, sulfur, carbon, hydrogen and nitrogen all conformed to the formula $Cu(EDA)_2SO_4$.

TABLE III

ANALYSES OF SOLID BIS (ETHYLENEDIAMINE) COPPER (II) SULFATE

| | % Calculated for $Cu(NH_2CH_2CH_2NH_2)_2 SO_4$ | Found % |
|---|---|---|
| Cu | 22.78 | 22.6 |
| $SO_4$ | 34.33 | 34.5[a] |
| C | 17.3 | 16.95 |
| H | 5.77 | 5.89 |
| N | 20.2 | 19.96 |
| Loss, 100° C. | 0 | 0.1 |

[a]Calculated from 11.5% S found.

Significant control of hydrilla was obtained with this material when used in treated ponds at copper concentrations as low as 0.5 ppm. based on copper in the water.

EXAMPLE 3

To a solution of 133 g. anhydrous EDA (98%) in 273 ml water was added slowly 117 g. copper hydroxide. The copper hydroxide dissolved rapidly. The addition was regulated to keep the temperature below 50° C. After complete dissolution of the solid, 273 ml water was added. The resulting solution was purple-blue as compared to the deep purple solution from the copper sulfate product. After stirring and cooling to 25° C., the following properties were found for the solution: 8.1% Cu, pH greater than 14, density 1.138, and viscosity 12 cps. After standing one week, a yellow-orange deposit was observed in the bottom of the container. The supernatant liquid was decanted and a new yellow deposit formed after another week storage.

EXAMPLE 4

In a similar procedure, as described in Example 3, 102 g. of copper hydrate (1 mole Cu) was added to 145 ml 91–93% ethylenediamine (EDA-2 moles) in 561 ml water. The hydrate dissolved rapidly when initially added to the EDA solution at 50° C. However, the temperature dropped and stirring for 4 hours at 30° C. was required to achieve complete dissolution. The final solution was a deep blue color. Properties of the liquid were: 8.15% Cu; pH greater than 14; density, 1.136 at 25° C.; and viscosity, 14.5.

As mentioned above bis(ethylenediamine) copper (II) have been prepared by the reaction of ethylenediamine with copper hydrate and copper hydroxide. However, the pH of these solutions is considerably higher (greater than 14) than the solutions made from copper sulfate (pH 9.0–11). These solutions are as a result less stable upon standing than those made with copper sulfate, but can be stabilized by adjusting the pH to between 9 to 11 by the addition of a mineral acid.

EXAMPLE 5

In a similar procedure, as described in Example 1, 131 grams of CSP were reacted slowly with 82 grams, 90% 1,2-propanediamine in aqueous solution. The reaction mixture rose to 69° C. After one hour the solution was diluted with water to give an 8.01% copper content. Other properties of the solution were: pH, 10.7; density at 25° C. 1.22 grams per cc; and viscosity, 20 cps.

Other copper complexes with aminoethylethanolamine, diethylenetriamine, triethylenetetramine, 1,3-propylenediamine, N,N'-dimethyl-1,3-propylenediamine, N-methyl-1-3 propylenediamine, and tetraethylene-pentamine, have also been prepared from copper sulfate and/or copper hydrate.

Generally, a ratio of about 2 to 1 of the amine to copper is used in a solution of 8% copper; the solubility is reduced with increasing amounts of higher alkylene di and triamines (water solubility decreases with each additional carbon atom in the alkylene herein, unless ionic groups are introduced). Copper content may range from 1–12%. An 8% copper solution is the preferred formulation; Table IV gives the chemical and physical properties for this preferred formulation.

TABLE IV

Bis (Ethylenediamine) Copper (II) Sulfate Complex solution and its properties for the use of it as an aquatic herbicide.

| Chemical Composition | Normal |
|---|---|
| Cu:EDA ratio | 1:2 |
| Cu metallic, % | 8:0 |
| EDA, % | 15.24 |
| $H_2O$, % | 64.67 |
| Physical Properties | |
| Density, g/cc 25° | 1.22 |
| pH | 10.0 |
| Viscosity cps | 14.5 |
| Color | Deep Purple |

EXAMPLE 6

As in Example 5, 131 grams CSP were added to an aqueous solution containing 96.2 grams N-methylethylenediamine. After stirring for 8 hours and diluting the solution to a copper content of 8.09%, the properties of the solution were as follows pH, 11.9; density at 25° C., 1.215 grams per cc; and viscosity at 25° C., 24 CPS.

Solutions containing 8% copper were prepared with ethylenediamine ratios of 2:1 mol EDA to copper using cupric chloride ($CuCl_2.2H_2O$), copper acetate ($Cu(CH_3CO_2)_2 \cdot H_2O$), copper nitrate ($Cu(NO_3)_2.3H_2O$) and copper sulfamate ($Cu(SO_3NH_2)_2$) solutions.

UTILITY OF THE INVENTION

The copper ethylene diamine complex may be employed by introducing the solution in any of the desired bodies of water in amounts up to from 0.1 ppm to 10 ppm expressed as copper. Generally from 0.5 ppm to 1.0 ppm is employed, although a range from 0.3 to 6 ppm is practical, broad range.

It has also been found that the fish toxicity (an undesirable phenomenon) of the herein disclosed algaecidal and herbicidal composition favorably compares with any of the existing algaecides and herbicides based on copper complexes. For example, the mortality, expressed as LC 50 (lethal concentration) in parts per million of copper of bluegill sunfish was 46.0 ppm at 24 hours and 30 ppm at 96 hours for the copper sulfate ethylene diamine complex. The improvement over the prior art complexes such as shown in U.S. Pat. No. 2,734,028 is about tenfold; same order of improvement is observed over copper sulfate.

A noticeable improvement was observed vis-a-vis the prior art compounds in respect to rainbow trout.

In respect to mammalian toxicity, the EDA-CSP complex has a low mammalian toxicity and comparable to the copper triethanolamine complex.

The algaecidal-herbicidal composition, as mentioned above, may be sold in the form of crystals, or slowly dissolving pellets or in a properly diluted water solution, or in conjunction with suitable extenders and diluents such as talc, clay, starch, gelatin and formulated with suitable surface active agents.

Because of greater stability, and use at higher pH values, the presently disclosed compositions are useful in irrigation systems in the Western United States because alkaline water is encountered in these systems.

The range of pH conditions within which the disclosed complexes are useful in between 7 to 11; a broader and still operative range is 6 to 12.

The algaecidal composition is effective against all common forms of algae, including filamentous algae, such as Cladophora and Spirogyra, planktonic algae such as Microcystis and Anabaena, branched algae such as *Chara vulgaris* and Nitella, swimming pool algae, commonly referred to as black, brown and red algae, and algae found in ponds such as Dictyosphaerium, Spirogyra, Oedogonium, Chlorococcum, Pithophora, Hydrodictyon, and Lyngbya.

TABLE V
ACTIVITY OF A SOLUTION OF EDA-CSP CRYSTALS FOR CERTAIN ALGAE SPECIES
Minimum Copper Concentration (ppm)

| Algae | Algistatic (Prevent Growth) | Algicidal (Kill Growth) |
|---|---|---|
| *Microcystis aeruginosa* | 0.01–0.02 | 0.01–0.02 |
| *Lyngbya versicolor* | 0.25 | 1.0 |
| *Pithophora oedogonium* | 0.04–0.08 | 0.08–0.17 |
| *Phormidium inundatum* | | |
| Allen's Medium (pH 7.0) | 0.83 | None |
| Gorham's Medium (pH 8.5) | 1.00 | None |
| *Chlorella pyrenoidosa* | | |
| Allen's Medium (pH 7.0) | None | None |
| Gorham's Medium (pH 8.5) | None | None |

Although in respect to some copper resistant algae the complexes described in the previously mentioned companion application is more effective, the overall herbicidal and algaecidal and algaestatic properties of the present compounds are outstanding, especially the herbicidal properties.

In respect to the herbicidal properties the following weeds, as an illustration, are subject to an effective attack by the disclosed compounds: Naiad, Vallisneria, Hydrilla, Milfoil, Hyacinths and *Egeria Densa*. Data for control of the noxious weed *Hydrilla verticillata* by typical examples of different copper diamine complexes are given in Table VI.

TABLE VI
EVALUATION OF COPPER DIAMINE COMPLEXES

| Solution | Cu Rate ppm | % Control of Hydrilla Weeks After Treatment | |
|---|---|---|---|
| | | 2 | 4 |
| $CuSO_4.2$(ethylenediamine) complex | 0.5 | 96 | 93 |
| $CuSO_4.2$(N—methyl ethylenediamine) complex | 0.5 | 93 | 93 |
| $CuSO_4.2$(1,2 propanediamine) complex | 0.5 | 98 | 97 |
| $CuSO_4.2$(1,3 propanediamine) complex | 0.5 | 15 | 37 |
| $CuSO_4.$(tetraethylenepentamine) complex | 0.5 | 20 | 23 |
| $Cu(OH)_2.2$(aminoethylethanolamine) complex | 0.5 | 70 | 75 |
| ethylenediamine (EDA) Tested at 5.0 ppm EDA Mixture | 0 | 0 | 0 |
| $CuSO_4.2$(ethylenediamine) 50% $Cu(OH_2).2$(triethanol- 50% amine) | 0.5 | 68 | 77 |
| $Cu(OH)_2.2$(ethylenediamine) complex | 0.5 | 92 | 88 |

TABLE VII
EVALUATION OF FIELD TEST PLOTS ALGAE AND WEEDS

| Plot[b] No. | Aqueous Tank | Organic Tank | 5 Week Evaluation |
|---|---|---|---|
| 1 | 16 gal. EDA-CSP[a] + 60 gal. water | 3.0 gal. SPRA-MATE 15.0 gal. xylene | 85% control 70% open water most impressive of all plots. Clean bottom, with small fragile sprigs of regrowth in ¼ of area. |
| 2 | 8 gal. EDA-CSP[a] + 4 gal. AQUA-K[d] + 60 gal. water | 3.0 gal. SPRA-MATE + 15.0 gal. xylene | 80–85% Control- Excellent control- bottom clean, surface covered with mass of yellow defoliated stems, completely mushy. |
| 3 | 8 gal. EDA-CSP[a] + 4 gal. DIQUAT[c] + 63 gal. water | 15.0 gal. xylene 3.0 gal. SPRA-MATE | 85–90% Control Plot still loose and coming off bottom, with compound remaining in area. Plot area is still free of hyacinths after 5 weeks. |

[a]Amounts of copper present 0.5, 0.25, and 0.25 ppm for plots 1 to 3 respectively.
[b]All treatment areas were two surface acres approximately five feet in depth.
[c]1,1' ethylene-2,2' dipyridinium dibromide
[d]Further combinations of the algaecide with AQUA-K ® as an adjuvant. (AQUA-K is 'The dipotassium salt of 3,6 endoxohexahydrophthalate'

TABLE VIII
EVALUATIONS OF FIELD TEST PLOTS - HERBICIDAL ACTIVITY

| No. | Surface Areas | Copper | Organic Herbicidals | Other Adjuvants | Invert | Organic Phase | Evaluation |
|---|---|---|---|---|---|---|---|
| 1 | 1 acre | EDA-CSP 18 gal.[a] | None | None | No | — | Excellent control (slight regrowth) |
| 2 | 1 acre | TEA-Cu 4 gal. | ALIQUAT ® 21[b,f] 3.2 gal. | None | No | — | Good control (regrowth) |
| 3 | 1 acre | EDA-CSP | NONE | None | No | — | Good con- |

TABLE VIII-continued
EVALUATIONS OF FIELD TEST PLOTS - HERBICIDAL ACTIVITY

| No. | Surface Areas | Copper | Organic Herbicidals | Other Adjuvants | Invert | Organic Phase | Evaluation |
|---|---|---|---|---|---|---|---|
| | | 20 gal.[a] | | | | | trol |
| 4 | 1 acre | EDA-CSP[b] 4 gal. | DIQUAT[g] 2 gal. | AMMATE ®[d] 25 lbs. | 0.5 gal. S-120[h] | Diesel | Excellent control |
| 5 | 1 acre | Cutrine ® [b,e] 4 gal. | DIQUAT 2 gal. | AMMATE 25 lbs. | 0.5 gal. S-120 | Diesel | Excellent control |
| 6 | Strip 9' × 400' | EDA-CSP[b] 4 gal. | DIQUAT 2 gal. | AMMATE 25 lbs. | 0-5 gal. S-120 | Diesel | Excellent control |

[a]Equivalent to 1 ppm copper on acre foot basis.
[b]Equivalent to 0.25 ppm copper on an acre foot basis.
[c]All invert treatments were applied through hoses dragged on the bottom; the inverts were formed as a tank mix prior to application.
[d]AMMATE also has herbicidal activity. Control due to AMMATE alone is unknown; AMMATE is ammonium sultemate.
[e]Reportedly the composition disclosed in U.S. Pat. No. 2,734,028.
[f]Aliquat 21 is trimethyl coco ammonium chloride.
[g]Identified above
[h]S-120 is an emulsifier available from the source identified below.

TABLE IX
RATINGS OF COMMERCIAL AND EXPERIMENTAL HERBICIDES FOR CONTROL OF EGERIA DENSA

| Treatments | Control Rating* |
|---|---|
| Bis(ethylenediamine) copper (II) (EDA-CSP), 8 gpa | 8.5 |
| Diquat 2 gpa + K-lox ®, 4 gpa | 6.5 |
| Diquat 2 gpa + EDA-CSP, 4 gpa | 5.5 |
| Diquat 2 gpa | 4.5 |
| K-lox, 8 gpa | 2.5 |
| Check | 1.5 |

K-lox is a complex of cupric hydroxide and triethanolamine of 8% copper solution, by weight.
*Means represent an average of visual ratings of two ½ acre plots where a rating of zero represents no egeria control and a rating of 10 represents complete control. gpa = gallons per surface area acre; 16 days after treatment.
Treatments were applied in a volume of 200 gpa through trailing hoses at an approximate depth of 6 ft.; copper is at 8% by weight of solution.

Field evaluations of the bis(ethylenediamine) copper complex have been very good. Excellent control of Hydrilla has been achieved with this complex when applied at 0.5 and 1.0 ppm copper or in combination with DIQUAT[R] or ENDOTHALL[R] disodium 3,6-endoxohexahydrophthalate. A solution of the EDA-CSP complex such as described in Example 2 can be inverted easily with emulsifiers such as SPRA-MATE (acid salt of a fatty amine from KDM Company, San Antonio, Texas) or S-120 (an emulsifier available from Standard Spray and Chemical Company, Lakeland, Fla.).

Results of field test evaluations of the bis(ethylenediamine) copper (II) complex used alone as a diluted liquid and with adjuvants are given in Tables VII, VIII, and IX. Table VII is a comparison of the copper ethylenediamine complex with and without the addition of an organic herbicide, DIQUAT[R] (1,1'-ethylene-2,2'-dipyridinium dibromide). Table VIII is the evaluation of field plots for the copper diamine complex as well as other copper-organic complexes with organic herbicides as adjuvants. Table IX compares the results obtained with the above named complex and other recommended standard herbicidal treatments for Egeria densa. The rate of the effective action of the EDA-CSP is noteworthy.

Corrosion studies show that a solution of EDA-CSP complex is slightly more corrosive than basic copper hydratetriethanol amine to aluminum and mild steel, but much less corrosive than a complex disclosed in U.S. Pat. No. 2,734,028 or copper sulfate.

In addition to the above desirable salts, the following copper salts are useful for forming the described complex: copper bromide, chlorate, citrate, formate, oxalate, benzoate, tartrate and the like.

What is claimed is:

1. A method for combatting aquatic weeds growing in waters, comprising dispersing in said waters an aqueous solution of a water soluble complex of a divalent copper salt and an amine of the formula:

$$R-RN-ALK-NRR$$

wherein ALK is alkylene of 2 or 3 carbon atoms and each R is independently hydrogen, methyl or ethyl, the amine to copper mol ratio being from 1:1 to 10:1, in an amount sufficient to provide on the basis of said waters a copper concentration of from 0.1 to 10.0 ppm, and thereby contacting said weeds with a herbicidally effective amount of said complex.

2. The method of claim 1 in which the copper salt is selected from the group consisting of copper hydroxide, acid copper sulfate, acid copper chloride, acid copper acetate, acid copper nitrate, and acid copper sulfamate.

3. The method of claim 2 in which the copper salt is acid copper sulfate or copper hydroxide.

4. The method of claim 3 in which the amine is ethylenediamine, N-methylethylenediamine or 1,2-propylenediamine.

5. The method of claim 4 in which the amine is ethylenediamine.

6. The method of claim 5 in which the mol ratio of amine to copper is 2:1.

7. The method of claim 6 in which the copper salt is copper sulfate pentahydrate.

8. The method of claim 7 in which Hydrilla Verticillata is combatted.

9. The method of claim 7 in which Egeria Densa is combatted.

10. The method of claim 1 in which the amine is ethylenediamine.

11. The method of claim 4 in which the amine is N-methylethylenediamine, the copper salt is copper sulfate and the mol ratio of such amine to the copper sulfate is 2:1.

12. The method of claim 4 in which the amine is 1,2-propylenediamine, the copper salt is copper sulfate and the mole ratio of such amine to the copper sulfate is 2:1.

13. The method of claim 1 or 5 in which the weeds as selected from the group consisting of Naiad, Vallisneria, Hydrilla, Milfoil, Hyacinths and *Egeria Densa*.

14. The method of claim 1, 5, 7 or 8 in which the amount of the complex is sufficient to provide on the bais of said waters a copper concentration of from 0.3 to 6.0 ppm.

15. The method of claim 1, 5, 7 or 8 in which the amount of the complex is sufficient to provide on the basis of said waters a copper concentration of from 0.5 to 1.0 ppm.

* * * * *